United States Patent
McAfee (10) Patent No.: US 8,597,331 B2
(45) Date of Patent: Dec. 3, 2013

(54) PROSTHETIC SPINOUS PROCESS AND METHOD

(75) Inventor: Paul McAfee, Sparks, MD (US)

(73) Assignee: Life Spine, Inc., Hoffman Estates, IL (US)

( * ) Notice: Subject to any disclaimer, the term of this patent is extended or adjusted under 35 U.S.C. 154(b) by 1491 days.

(21) Appl. No.: 11/296,470

(22) Filed: Dec. 8, 2005

(65) Prior Publication Data

US 2006/0161154 A1  Jul. 20, 2006

Related U.S. Application Data

(60) Provisional application No. 60/634,807, filed on Dec. 10, 2004.

(51) Int. Cl.
*A61F 2/30* (2006.01)

(52) U.S. Cl.
USPC .......................... 606/248; 606/264; 623/17.16

(58) Field of Classification Search
USPC ......... 606/248, 249, 250, 251, 252, 253, 254, 606/255, 256, 257, 258, 259, 260, 261, 262, 606/263, 264, 265, 266, 267, 268, 269, 270, 606/271, 272, 273, 274, 275, 276, 277, 278, 606/279; 623/17.16
See application file for complete search history.

(56) References Cited

U.S. PATENT DOCUMENTS

| | | | | |
|---|---|---|---|---|
| 4,653,481 A * | 3/1987 | Howland et al. | ............... | 606/261 |
| 5,387,212 A * | 2/1995 | Yuan et al. | ..................... | 606/264 |
| 5,437,669 A * | 8/1995 | Yuan et al. | ..................... | 606/278 |
| 5,476,463 A * | 12/1995 | Boachie-Adjei et al. | ..... | 606/264 |
| 5,984,922 A * | 11/1999 | McKay | ....................... | 606/86 A |
| 6,419,703 B1 * | 7/2002 | Fallin et al. | ................ | 623/17.11 |
| 6,554,831 B1 * | 4/2003 | Rivard et al. | .................. | 606/253 |
| 6,626,909 B2 * | 9/2003 | Chin | ............................. | 606/276 |
| 6,669,729 B2 * | 12/2003 | Chin | ......................... | 623/17.11 |
| 7,011,685 B2 * | 3/2006 | Arnin et al. | ................. | 623/17.16 |
| 7,163,538 B2 * | 1/2007 | Altarac et al. | ............. | 606/86 A |
| 7,282,065 B2 * | 10/2007 | Kirschman | ................ | 623/17.15 |
| 2002/0026193 A1 * | 2/2002 | Barker et al. | ................... | 606/61 |
| 2002/0029039 A1 * | 3/2002 | Zucherman et al. | ............ | 606/61 |
| 2003/0004572 A1 * | 1/2003 | Goble et al. | ............... | 623/17.11 |
| 2003/0171750 A1 * | 9/2003 | Chin | ............................... | 606/61 |
| 2004/0015166 A1 * | 1/2004 | Gorek | ............................ | 606/61 |
| 2004/0186472 A1 * | 9/2004 | Lewis et al. | ..................... | 606/61 |
| 2005/0033434 A1 * | 2/2005 | Berry | ......................... | 623/17.14 |
| 2005/0192671 A1 | 9/2005 | Bao | | |
| 2005/0245929 A1 * | 11/2005 | Winslow et al. | ................ | 606/61 |
| 2006/0015181 A1 * | 1/2006 | Elberg | ......................... | 623/16.11 |
| 2006/0036246 A1 * | 2/2006 | Carl et al. | ....................... | 606/61 |
| 2006/0241601 A1 * | 10/2006 | Trautwein et al. | .............. | 606/61 |
| 2008/0234735 A1 * | 9/2008 | Joshi | ............................. | 606/247 |

OTHER PUBLICATIONS thefreedictionary.com, accessed Jul. 13, 2010, definition for "rod".*

* cited by examiner

*Primary Examiner* — Jan Christopher Merene
(74) *Attorney, Agent, or Firm* — Foley & Lardner LLP (57) ABSTRACT

A prosthetic spinous process includes a member and a plurality of crosslinking rods connected to the member at an angle relative to each other, wherein the member includes at least one opening therethrough.

24 Claims, 9 Drawing Sheets

PROSTHETIC SPINOUS PROCESS AND METHOD

This application claims priority of provisional application Ser. No. 60/634,807, Filed Dec. 10, 2004

BACKGROUND OF THE INVENTION

Field of the Invention

The present invention relates to prosthetic medical devices and methods. In particular, the present invention relates to prosthetic medical devices and methods for the human vertebral column.

DETAILED DESCRIPTION OF SEVERAL EMBODIMENTS

One embodiment provides a device or method for attachment and/or reconstruction of a posterior aspect of the spinal column.

In one embodiment, a prosthetic spinous process device and method are provided for anchoring one or more artificial ligaments, cushions, tensile elements, spinal reconstructive devices, posterior artificial ligaments, posterior dynamic systems, posterior arthrodesis stabilization systems, or the like. A spinous process may be defined as an outward projecting part of a vertebra, sacrum or coccyx.

One embodiment is suited for applications including stabilization and arthrodesis of segments of the vertebral column in degenerative pathologies of the spine. One embodiment may be used with prior laminectomy, removal of the posterior elements, post-laminectomy syndrome, spina bifida, prior resection of the posterior spinal elements, DDD, and post-diskectomy syndrome. In addition, while not being limiting, at the base of the spinal column at the S1 or first sacral vertebra there is often missing bone (spina bifida occulta) or atrophic bone, and one embodiment is suited for use in these cases as well.

One embodiment provides an easily adjustable structure for securely attaching one or more posterior dynamic systems. When in place, the prosthetic spinous process is offset dorsally and in a more caudal position than pedicle screws attaching the prosthetic spinous process to an aspect of the spinal column. In this embodiment, the potential complications associated with conventional systems, e.g., cutting out and penetrating lumbar nerve roots, dura mater, or spinal soft tissue, are reduced or avoided entirely.

Figure 1:
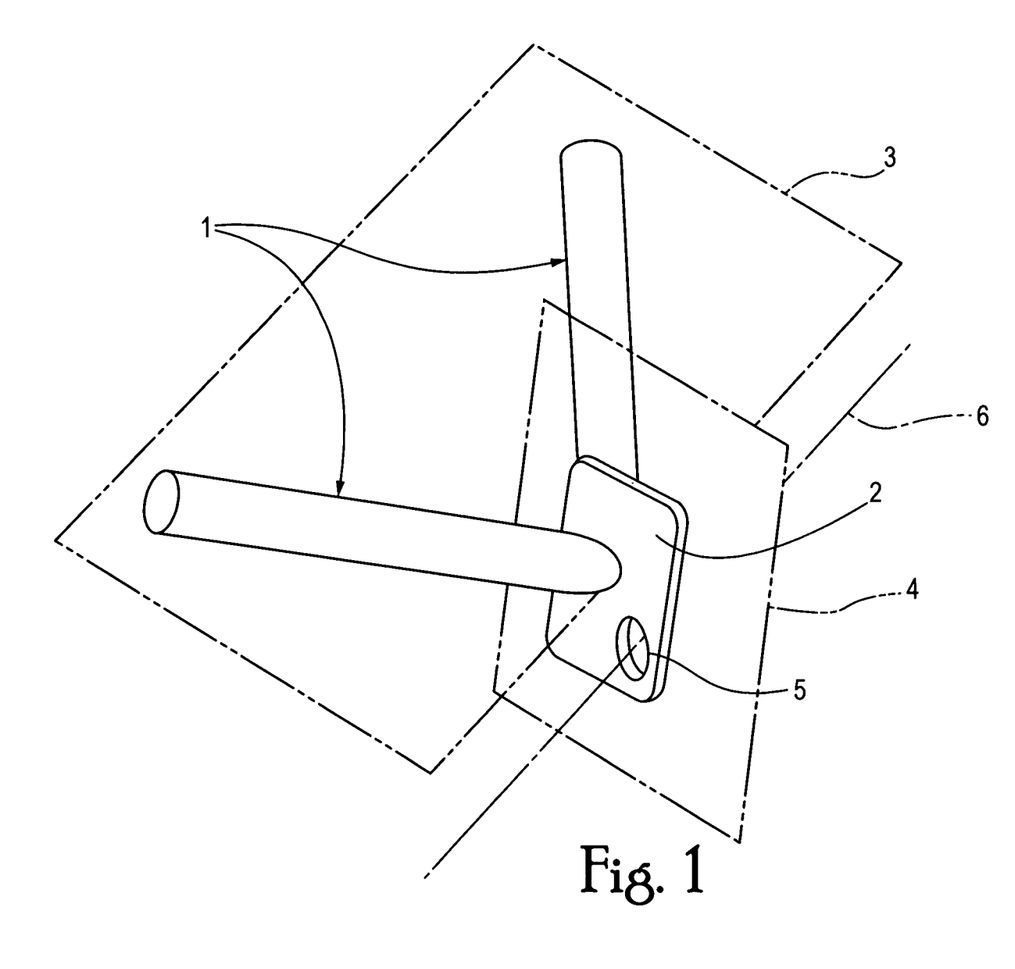
FIG. 1 shows a perspective drawing of one embodiment of the present invention.

As illustrated in FIG. 1, one embodiment of the prosthetic spinous process includes two crosslinking rods 1 joined at a first angle having a member 2 at their vertex. The plane defined by the crosslinking rods 1, i.e., the first plane 3, is substantially coplanar with the long axes of both crosslinking rods 1, i.e., that the long axes of both crosslinking rods 1 lie in the first plane 3.

The device additionally contains a member 2, the body of which has a plane of symmetry, e.g., is substantially symmetrical about a single plane. The second plane 4 is substantially coplanar with this plane of symmetry.

In the device, the first plane 3 and the second plane 4 are disposed at a second angle of 80 to 100 degrees relative to one another. This range includes 80, 81, 82, 83, 84, 85, 86, 87, 88, 89, 90, 91, 92, 93, 94, 95, 96, 97, 98, 99, and 100 degrees. In one embodiment of the device, the first plane 3 and the second plane 4 are normal to one another, i.e., they are disposed at right angles with respect to one another.

To solve the problem of varying interpedicular distance, the two crosslinking rods 1 attach to pedicle screws 9 (See FIG. 2) in one embodiment. The pedicle screws can be inserted percutaneously, or through minimally invasive techniques. In one embodiment, the surgeon has the freedom to cut off the excess of one or more of crosslinking rods 1, which allows better adjustability and less inventory.

The member 2 further includes at least one opening 5 therethrough. The opening 5 defining an axis can be disposed normal to the second plane and above or below the first plane.

Another embodiment provides a method, which includes contacting the device discussed herein with a part of a human body. For example, the device can provide a prosthetic spinous process at any of the human vertebrae.

In one embodiment, the device provides a prosthetic spinous process for one or more of the lumbar vertebrae L1, L2, L3, L4, or L5, or sacral vertebrae S1, S2, S3, S4, or S5.

The crosslinking rods 1 can be cylindrical, each having an independent length and diameter. The respective lengths and diameters of the crosslinking rods 1 may be the same or different. The lengths can be greater than the diameters. The crosslinking rods 1 can have identical diameters.

The crosslinking rods 1 may have any suitable diameter ranging from 2 to 15 mm. This range includes 2, 3, 3.5, 3.75, 4, 4.25, 4.5, 4.75, 5, 5.25, 5.5, 5.75, 6, 6.25, 6.35, 6.5, 6.75, 7, 7.25, 7.5, 7.75, 8, 8.5, 9, 9.5, 10, 10.5, 11, 12, 13, 14, and 15 mm, and any diameter therebetween. For example, such diameters can include ³⁄₁₆", ¼", ⅜" and 5.5 mm.

The crosslinking rods 1 may have an aspect ratio of length/diameter ranging from 200 to 1. This range includes 200, 175, 150, 125, 100, 90, 80, 70, 60, 50, 40, 30, 20, 10, 9, 8, 7, 6, 5, 4, 3, 2, and 1, any combination thereof, and any aspect ratio therebetween.

The crosslinking rods 1 may meet at any first angle of from 110 to 170 degrees, which range includes 110, 120, 125, 130, 133, 135, 137, 139, 140, 145, 150, 151, 152, 153, 154, 155, 156, 157, 158, 159, 160, 161, 163, 165, 167, and 170 degrees, and any angle therebetween.

The second plane 4 defined by member 2 may bisect the first angle defined by the crosslinking rods 1. In one embodiment, the second plane 4 bisects the first angle defined by the crosslinking rods and is normal to the first plane 3.

The crosslinking rods 1 and/or member 2 may be made of any material, such as metal, alloy, plastic, composite, biomaterial, or the like. The crosslinking rods 1 and/or member 2 may or may not have one or more coatings to enhance their mechanical or electrical properties, or to enhance their biocompatibility. Non-limiting examples of suitable metallic materials include titanium, stainless steel, cobalt chrome, ceramic, bioabsorable materials, and the like. Non-limiting examples of plastic materials include PEEK (polyetheretherketone), PIIKEK, and other related composites, polycarbonate, polyurethane, silastic, rubber, polyethylene, UHMWPE (ultrahigh molecular weight polyethylene), or plastic. Combinations of materials are possible.

The device may be attached to any part of the body as deemed appropriate to one of ordinary skill in this art. The device can be attached to one or more human bony parts. The device can be attached to one or more bones in the human vertebral column. These include any of the lumbar vertebrae L1, L2, L3, L4, and L5, or sacrum S1, S2, S3, S4, and S5, or any combination thereof.

The device can be attached to the body by any technique known in the art. The attachment means may suitably include one or more pedicle screws, polyaxial pedicle screws, monoaxial pedicle screws, cannulated pedicle screws, solid pedicle screws, screws which are placed or fixed anywhere on the spine, vertebral body screws, iliac crest screws, facet screws, laminar hooks, pedicle hooks, circumferential spinal fixation wires, and any combination thereof. The device may be affixed internally or externally. The device may be inserted percutaneously if desired.

In one embodiment, the device is attached to bone with two or more pedicle screws. Pedicle screws are known in the art and are typically threaded bone screws adapted for placement to and/or through any of the lamina, pedicle and/or the vertebral body. These screws may be affixed internally or externally, and they may be inserted percutaneously, if desired. The pedicle screws may be affixed directly or indirectly to or through one or more of the crosslinking rods 1 of the device. Alternatively, the crosslinking rods 1 are affixed directly or indirectly to or through the screws. The screws are screwed into a bony part along the vertebral column.

The pedicle screw may have a head or tulip that can rotate about many axes to accommodate various anatomical conditions and positions. This type of screw is called polyaxial. Monoaxial screws, e.g., those that do not have a rotating head, may also be used, however. The polyaxial screw may be solid or cannulated. Cannulated screws have a hollow center, which allows the surgeon to place the screw over a previously inserted guide pin. Non-limiting examples of polyaxial pedicle screws include those sold under the names PATH-FINDER™, available from Spinal Concepts, a division of Abbott Laboratories, MOSS MIAMI™, MONARCH™, and EXPEDIUM™, available from DePuy Spine, Inc., XIA™, available from Stryker™ Spine, and CD HORIZON™ and CD HORIZON SEXTANT™ systems available from Medtronic Sofamor Danek.

The sacrum affords a much larger diameter pedicle screw than other spinal levels. Accordingly, in one embodiment, a screw-within-a-screw construct may be used, which locks the crosslinking rod 1 to the pedicle screw. The pedicle of S1 can often accommodate a pedicle screw of diameter 8.5 mm. Accordingly, in one embodiment, the pedicle screw may be a cannulated or hollow screw, and a locking screw passing through the crosslinking rod 1 (with, for example, a corresponding 3 mm hole therein), could be fixed by a second 3 mm diameter locking screw which passes through the hole and into the 7.5 mm or 8.5 mm diameter sacral S1 pedicle screw.

Figure 8:
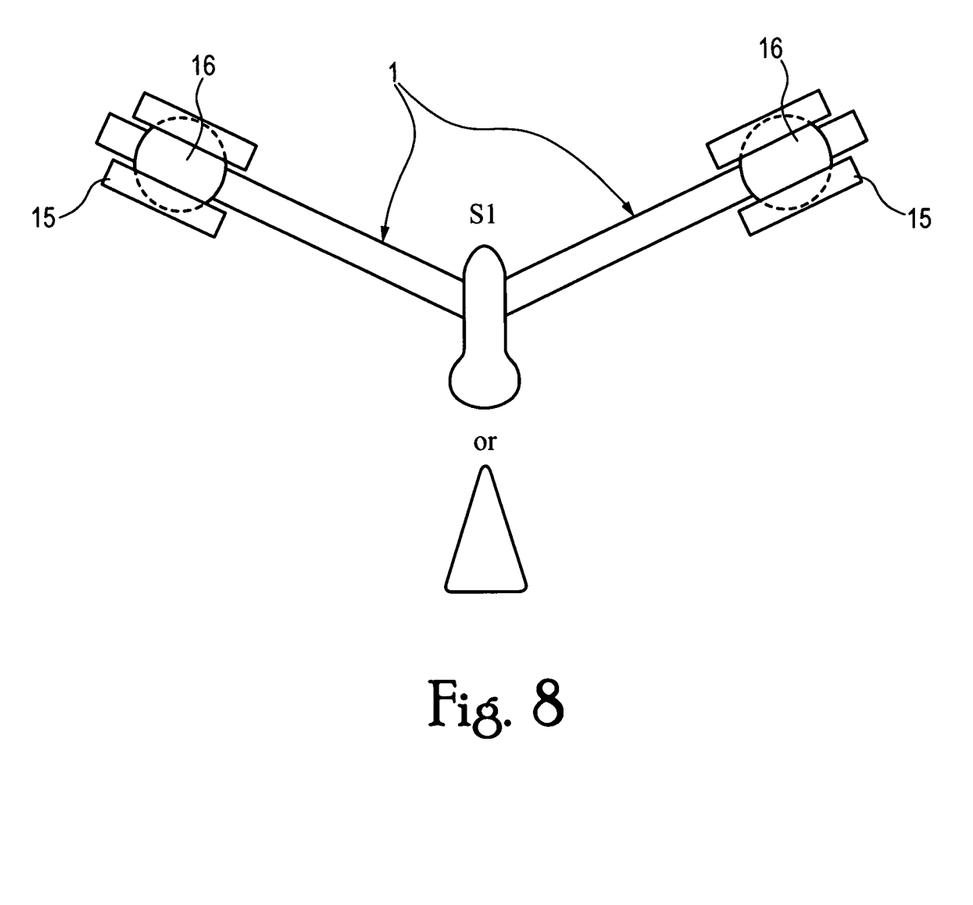
FIG. 8 shows a dorsal view of one embodiment of the invention.

The distal end of the crosslinking rod 1, at any distance away from the vertex of the device, may be plain or may be modified to improve its attachment to the pedicle screw. In one embodiment, one or both of the crosslinking rods 1 may be adapted to allow the surgeon to cut off excess crosslinking rod 1 as appropriate. In another embodiment, the distal end of one or both of the crosslinking rods 1 may have a ball 16 (See FIG. 8), e.g., for a ball and socket joint, or an elliptical enlargement to allow a tighter fit into the tulip 15 of the screw. As shown in FIG. 8, the ball 16 or elliptical enlargement on the distal ends of the crosslinking rods 1 accommodate a corresponding socket connection in the tulip 15 or accommodate a corresponding enlargement in the tulip 15.

In one embodiment, the crosslinking rod 1 may have one or more cannulations 14 (See FIG. 6), e.g., holes or slots therethrough, in view of accommodating one or more guidewires 13 to help guide the crosslinking rod 1 into the tulip 15 or cannulated screw 12. In one embodiment, both the screw 12 and crosslinking rod 1 may be cannulated to facilitate percutaneous or minimally invasive insertion.

Figure 6:
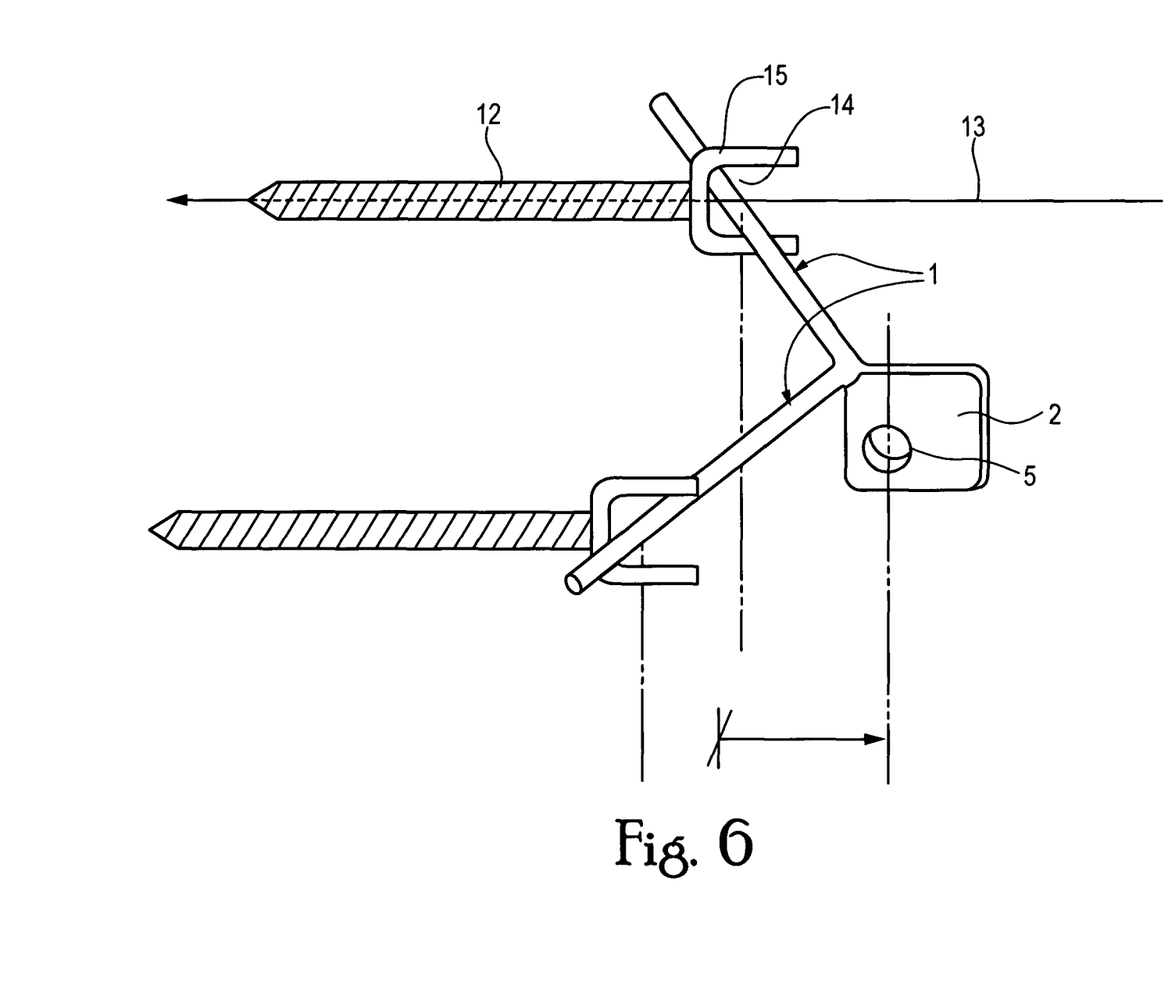
FIG. 6 shows a lateral offset view of one embodiment of the invention.

The ball-shaped portion or enlargement 16 to the diameter of the crosslinking rod 1 may desirably correspond to a ball-and-socket type receptacle on the tulip 15. For ease of percutaneous insertion, the pedicle screw can be cannulated and the one or both of the crosslinking rods 1 can have a hole, a slot, or an oblong hole where the guide wire or guiding suture or guiding mechanism can be threaded through the (or attached to the crosslinking rod 1 by another mechanism) transverse crosslinking rod 1. FIG. 6 shows one embodiment of a cannulated polyaxial screw 12 with a guidewire 13. As shown in FIG. 6, the crosslinking rod 1 may have a hole 14 or slot in it to help guide the crosslinking rod 1 into the tulip 15 of the polyaxial screw. This allows a more secure approximation between the crosslinking rod 1 and the pedicle screw, which can be placed percutaneously or through a minimal exposure type surgical approach.

Figure 5:
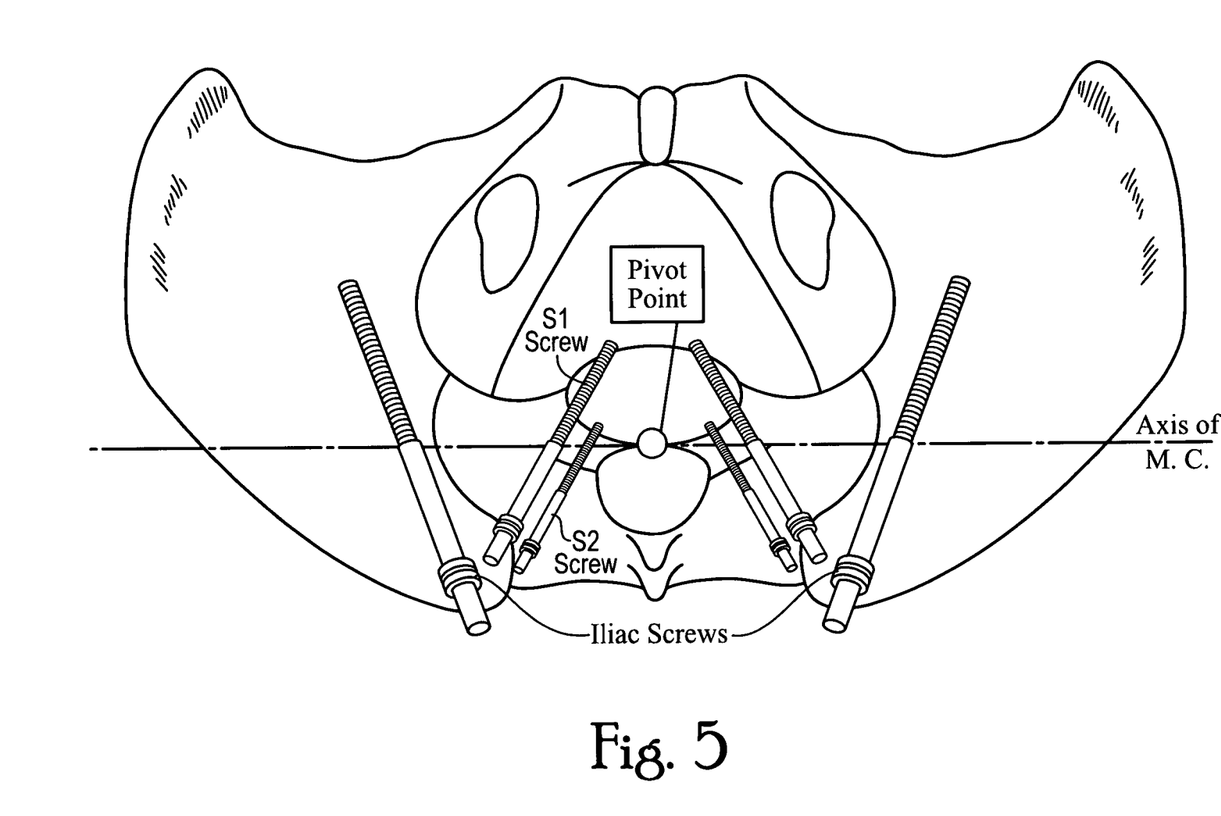
FIG. 5 shows one embodiment of attachment screws that can be used with the present invention.

The two pedicle screws may be affixed in a converging, triangular transverse fashion, or they may be affixed in a diverging manner. In one embodiment, the pedicle screws are cross-linked together in a triangular fashion. This triangulation of the pedicle screws improves the pull-out strength because the pull-out strength is determined by the area of bone between the screws rather than simply the bone within the screw threads. Triangulation thus leads to improved cyclical pull-out strength. FIG. 5 shows one embodiment of pedicle screw fixation.

In one embodiment, S1 pedicle screws are used. Non-limiting possible attachment points of the screws include the medial aspect of the sacrum at S1, the medial aspect of the sacrum at S2, or the laterally diverging iliac crest (See FIG. 5). Without being limiting, any of these three trajectories and locations for the screws may be suitably used as the anchoring points for the artificial or prosthetic spinous process.

Figure 7:
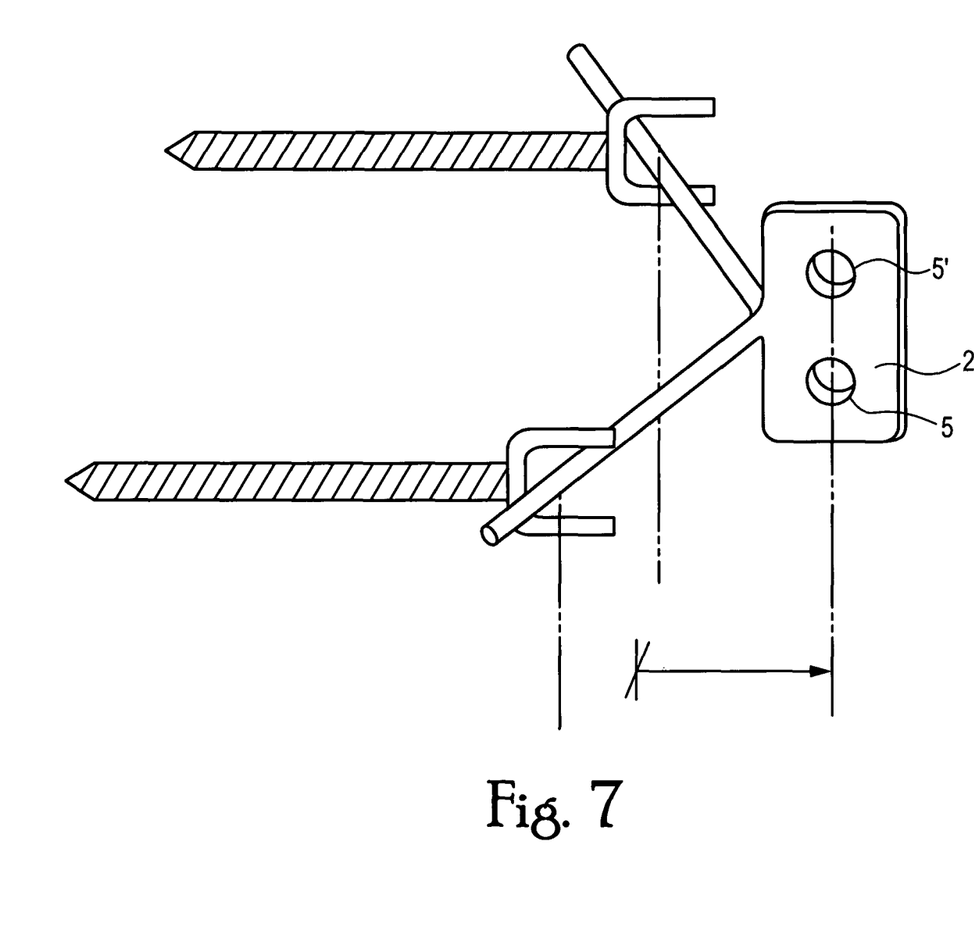
FIG. 7 shows a lateral offset view of one embodiment of the invention.

The member 2 includes at least one opening 5. The opening 5 defines an axis 6 that is disposed above, below or at the first plane 3, and parallel to the first plane 3. The axis 6 is also substantially normal to the second plane 4, defined by the member 2. The member 2 may optionally include one or more additional opening 5' (See FIG. 7). The opening 5' can be above, below or at the same level as first plane 3. The shape of the opening 5 is not particularly limiting, as long as it passes through the member 2. The opening 5 may be circular, ovoid, rectangular, square, triangular, slotted, or any combination thereof.

The opening 5 can be sufficient to allow one or more tensile elements, e.g., a polyester or P.E.T. band to pass therethrough and connect the device to either to an opening 5 on another prosthetic spinous process device, to another part of the body, to another part of the vertebral column, or to different device entirely. The tensile element may be connected to any combination other connections, parts, and devices as appropriate.

In this regard, one embodiment may be suitably used with and/or connected to various types of spinal stabilization systems, intervertebral implants, and the like. Suitable non-limiting examples include the WALLIS™ and DIAM™ Spinal Stabilization Systems from Medtronic, and those such as disclosed in U.S. Pat. No. 6,761,720, and U.S. Patent Application Pub. No. 2004/0024458, for example.

At least a portion of the opening 5 can available either above or below or both the device to enhance applicability to more cranial or cephalad vertebral levels, e.g., L1 to L5. In another embodiment, at least a portion of the opening 5 is available above or below the point on the member 2 where the crosslinking rods 1 attach to the member 2. The opening 5 should be available on the cranial or superior aspect of the prosthetic spinous process as well as on the caudal or inferior aspect of the prosthetic spinous process. In view of improved utility at vertebral levels in the lumbar spine the opening 5 can be available below, above or both above and below (cephalad and caudad) to the prosthetic spinous process.

Figure 4:
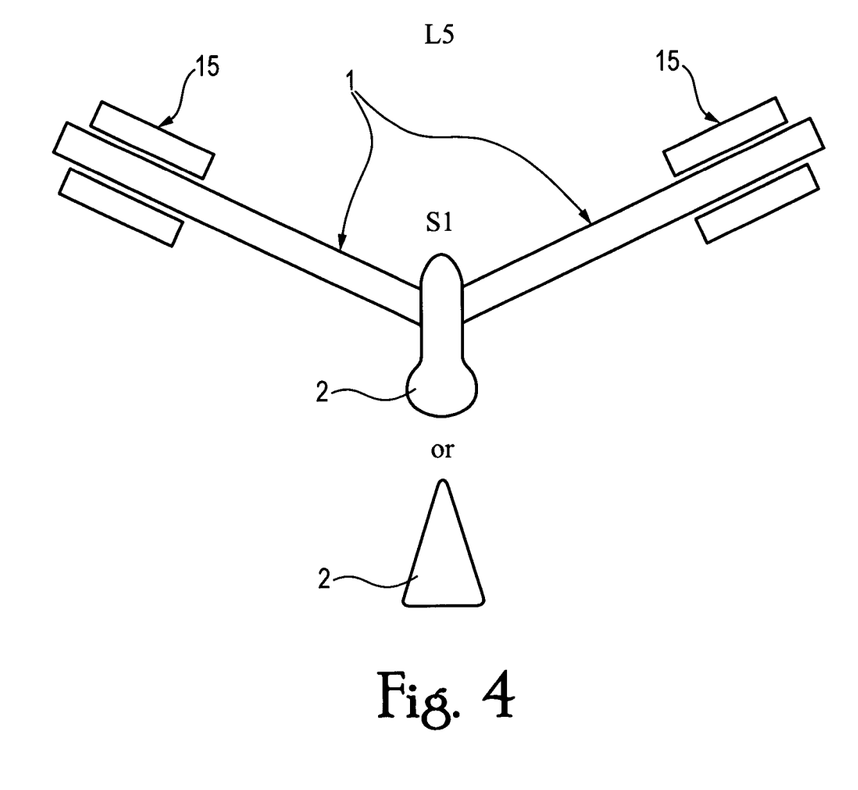
FIG. 4 shows a dorsal view of one embodiment of the present invention.

The shape of the member 2 is not particularly limiting, so long as it has a portion that lies either above, below, or above and below the first plane 3, and has at least one opening 5 that lies either above or below the first plane 3. The member 2 may have shape that, when viewed along a dorsal midline view, increases in thickness in the direction of cephlad to caudad. The increase in thickness may be constant, to effect a triangular projection, or the increase in thickness may be variable, to effect a bulbous projection (See FIGS. 4 and 8). When viewed along the axis 6, the member may have a parallelpiped, square, rectangular, ovoid, circular, triangular, or other polygonal shape as appropriate.

Figure 9:
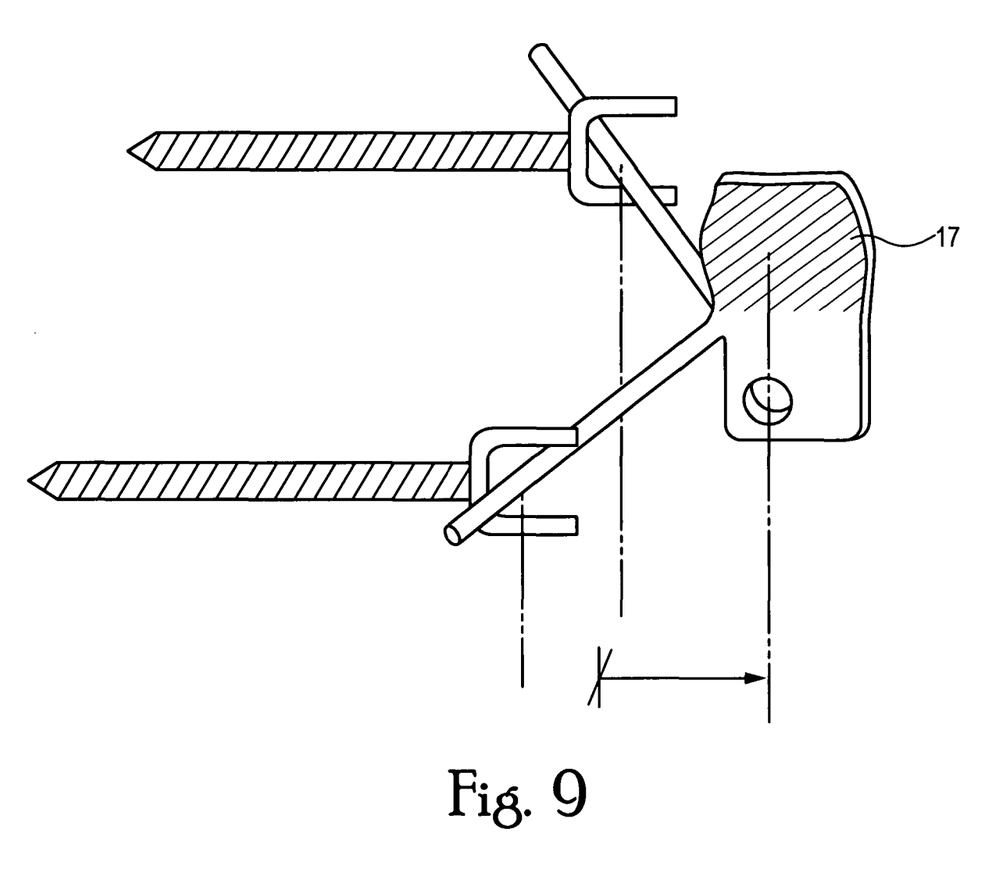
FIG. 9 shows a lateral offset view of one embodiment of the invention.

In one embodiment, the member 2 may additionally include a compressible material 17. The compressible material 17 can function as an interspinous or intervertebral distraction, cushion, or fixation, interspinous bumper, wedge, WALLIS™ device, DIAM™ device, or, spongy interspinous material (See FIG. 9), attached thereto, or in contact therewith, or working in concert therewith. The material may either be integrally bonded to the member 2 body, or it may be intraoperatively attached by the surgeon. Integral bonding can be used in view of strength, convenience, better fit, more press fit and better contouring between the prosthetic spinous process and the compressible material. The compressible material may be one or more of PEEK (polyetheretherketone), plastic, polycarbonate, polyurethane, silastic, rubber, or UHMWPE (ultrahigh molecular weight polyethylene). Combinations are possible.

One embodiment provides a prosthetic S1 spinous process, wherein the member 2 becomes thicker as the midline dorsal projecting element goes from cephlad to caudad. This desirably gives more compression resistance to a midline "bumper", sleeve, or interspinous process wedge.

Figure 2:
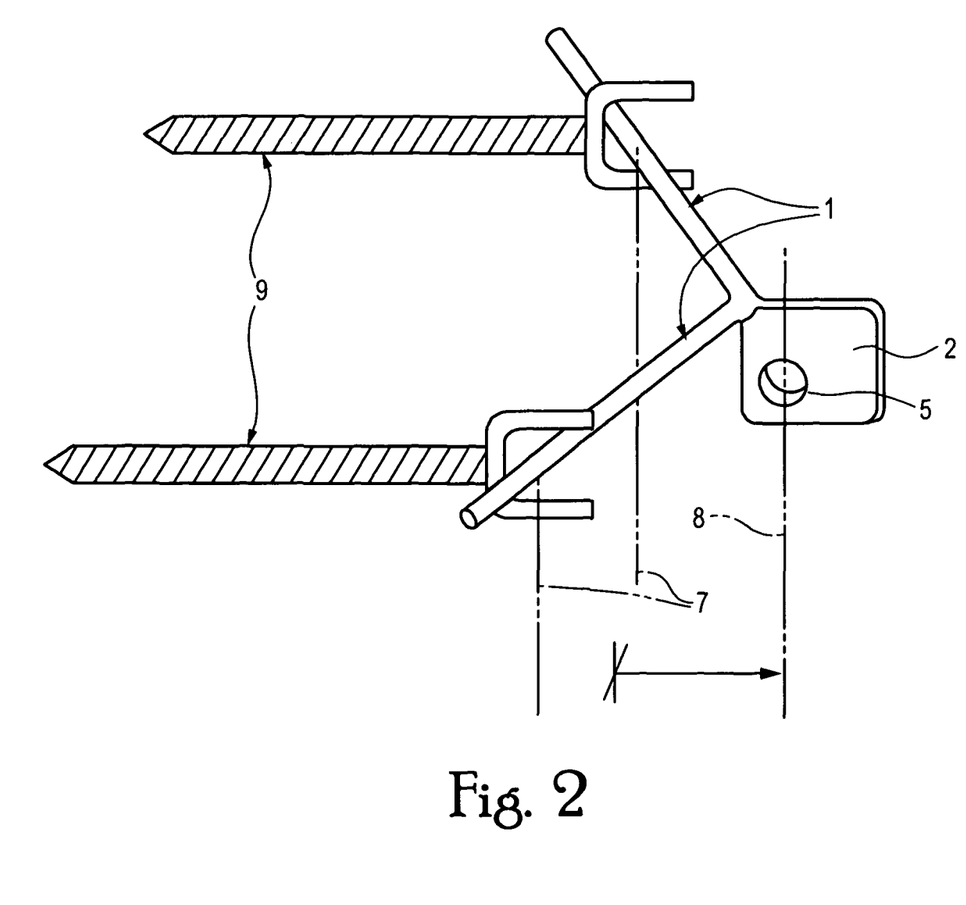
FIG. 2 shows a lateral offset view of one embodiment of the present invention.
Figure 3:
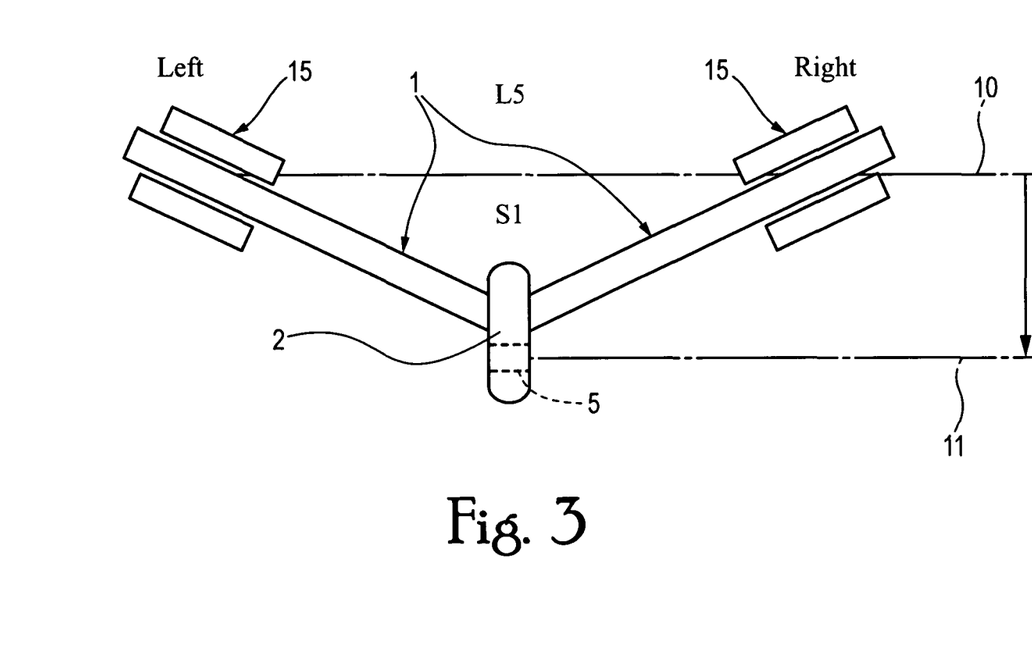
FIG. 3 shows a dorsal view of one embodiment of the present invention.

One embodiment provides a crosslink with a posterior projection beyond the axis of the crosslinking rods 1. One embodiment provides a prosthetic spinous process that projects farther posteriorly than the coronal plane of the pedicle screws. FIG. 2 shows a lateral offset view of one embodiment. As shown in FIG. 2, a plane between dashed lines 7 shows a coronal plane of the pedicle screws. Dashed line 8 shows a posterior projection of the opening 5 away from the coronal plane. An embodiment of polyaxial screws 9 is shown. As shown in FIG. 3, a dashed line 10 shows one possible screw position. Dashed line 11 shows one possible cephlad projection of the opening 5 away from the screw position 10.

One embodiment provides a prosthetic spinous process in which the apex or vertex of the two transverse crosslinking rods 1 joining together in the midline is more dorsal than the pedicle screw heads. This may give more room for the dura at S1 which is in this location.

One embodiment enables the tulip portion 15 of the connecting pedicle screws to be open and face the transverse direction rather than the longitudinal direction, in contrast to conventional devices.

All or any portion of the device may have one or more coatings to effect a more biocompatibile surface, bioinert surface, or both. Non-limiting examples of coatings include tantalum, niobium, zirconium, titanium, and platinum bioactive glass, hydroxyapatite, recrystallized hydroxyapatite, zirconium oxide, aluminum oxide, resorbable bioceramic, pyrolytic carbon, hydrophilic coating, hydrophobic coating, silicone-based coating, titanium nitride coating, radiopaque coating, ceramic coating, antimicrobial coating, ion implantated surface, radioactive coating, polyurethane, silicone, polyester, polycarbonate, polyethylene, polyvinyl chloride, polypropylene, acrylate, (meth)acrylate, biodegradable copolymer, copolymer surface coating and/or PTFE coating as appropriate. Combinations are possible.

The entire contents of each of the patents, applications, and articles cited herein is hereby incorporated by reference, the same as if set forth at length.

What is claimed is:

1. A prosthetic spinous process, comprising:
   a member having a first surface, a second surface generally opposite the first surface, and an opening extending between the first surface and the second surface, where the opening defines an axis substantially normal to a plane of symmetry defined between the first and second surfaces,
   a plurality of crosslinking rods defining a first angle having a vertex, the plurality of crosslinking rods being connected to the member at the vertex and comprising a first generally cylindrical crosslinking rod extending from the first surface and a second generally cylindrical crosslinking rod extending from the second surface; and
   a pedicle screw adjustably attached to each of the rods, the pedicle screws being constructed and arranged to be attached to an aspect of a spinal column wherein the member is offset dorsally and in a more caudal position than the pedicle screws.

2. The prosthetic spinous process of claim 1, wherein the crosslinking rods define a rod plane.

3. The prosthetic spinous process of claim 2, wherein the rod plane and the plane of symmetry are disposed at a second angle of 80 to 100 degrees relative to one another.

4. The prosthetic spinous process of claim 3, wherein the second angle is 85 to 95 degrees.

5. The prosthetic spinous process of claim 3, wherein the second angle is 90 degrees.

6. The prosthetic spinous process of claim 2, wherein the opening is disposed above or below the rod plane.

7. The prosthetic spinous process of claim 2, wherein the opening is disposed above the rod plane.

8. The prosthetic spinous process of claim 2, wherein the opening is disposed below the rod plane.

9. The prosthetic spinous process of claim 1, wherein the angle of the rods relative to each other is 110 to 170 degrees.

10. The prosthetic spinous process of claim 1, wherein the opening is adapted to allow one or more tensile elements to pass therethrough.

11. The prosthetic spinous process of claim 1, wherein the member has a parallelpiped, square, rectangular, ovoid, circular, or triangular shape.

12. The prosthetic spinous process of claim 1, wherein the member further comprises at least one second opening.

13. The prosthetic spinous process of claim 1, wherein the prosthetic spinous process is connected to at least one artificial ligament, cushion, tensile element, spinal reconstructive device, posterior artificial ligament, posterior dynamic system, posterior arthrodesis stabilization system, or a combination thereof.

14. The prosthetic spinous process of claim 1, wherein the opening is available at a vertebral level above a vertebral level of the prosthetic spinous process.

15. The prosthetic spinous process of claim 1, wherein the opening is available at a vertebral level below a vertebral level of the prosthetic spinous process.

16. The prosthetic spinous process of claim 1, wherein at least a portion of the opening is available at a vertebral level above a vertebral level of the prosthetic spinous process, below the vertebral level of the prosthetic spinous process, or both.

17. The prosthetic spinous process of claim 1, wherein the member has a shape that increases in thickness in the direction of cephlad to caudad when viewed along a dorsal midline view.

18. The prosthetic spinous process of claim 1, wherein at least a portion of the prosthetic spinous process further comprises a coating selected from the group consisting of polyurethane, silicone, polyester, polycarbonate, polyethylene, polyvinyl chloride, polypropylene, PTFE, and a combination thereof.

19. The prosthetic spinous process of claim 1, wherein the crosslinking rods are configured to allow removal of any excess length of the crosslinking rods to adjust for varying interpedicular distances.

20. A prosthetic spinous process, comprising:
a member having a first surface, a second surface generally opposite the first surface, and an opening extending between the first surface and the second surface, where the opening defines an axis substantially normal to a plane of symmetry defined between the first and second surfaces, the member further comprising at least one compressible material;
a plurality of crosslinking rods defining a first angle having a vertex, the plurality of crosslinking rods being connected to the member at the vertex and comprising a first generally cylindrical crosslinking rod extending from the first surface and a second generally cylindrical crosslinking rod extending from the second surface; and
a pedicle screw adjustably attached to each of the rods, the pedicle screws being constructed and arranged to be attached to an aspect of a spinal column wherein the member is offset dorsally and in a more caudal position than the pedicle screws.

21. The prosthetic spinous process of claim 20, wherein the compressible material of the member is integrally bonded to the member.

22. The prosthetic spinous process of claim 20, wherein the compressible material functions as an interspinous distraction, an intervertebral distraction, a cushion, a fixation, an interspinous bumper, a wedge, a WALLIS™ device, a DIAM™ device, or a spongy interspinous material.

23. The prosthetic spinous process of claim 20, wherein the compressible material comprises polyetheretherketone, plastic, polycarbonate, polyurethane, silastic, rubber, ultrahigh molecular weight polyethylene, or a combination thereof.

24. The prosthetic spinous process of claim 20, wherein the compressible material comprises at least one of polyetheretherketone, plastic, polycarbonate, polyurethane, silastic, rubber, ultrahigh molecular weight polyethylene, or a combination thereof.

* * * * *